(12) United States Patent
Moisio

(10) Patent No.: US 6,297,882 B1
(45) Date of Patent: Oct. 2, 2001

(54) METHOD AND APPARATUS FOR MEASURING PAPER COLOR

(75) Inventor: Hannu Moisio, Kangasala (FI)

(73) Assignee: Metso Paper Automation Oy, Tampere (FI)

( * ) Notice: Subject to any disclaimer, the term of this patent is extended or adjusted under 35 U.S.C. 154(b) by 0 days.

(21) Appl. No.: 09/551,679

(22) Filed: Apr. 20, 2000

Related U.S. Application Data

(63) Continuation of application No. PCT/FI98/00770, filed on Sep. 29, 1998.

(30) Foreign Application Priority Data

Jan. 10, 1997 (FI) .......................................... 973856

(51) Int. Cl.⁷ .................................................. B01J 29/46
(52) U.S. Cl. ........................................... 356/429; 242/563
(58) Field of Search .................................... 356/429, 430, 356/431, 238.1, 238.2; 242/563

(56) References Cited

U.S. PATENT DOCUMENTS

| | | |
|---|---|---|
| 4,715,715 | 12/1987 | Howarth et al. . |
| 4,865,456 | 9/1989 | Mast et al. . |
| 5,047,652 | 9/1991 | Lisnyansky et al. . |
| 5,082,529 | 1/1992 | Burk . |
| 5,592,294 * | 1/1997 | Ota et al. ............................. 356/402 |
| 5,758,982 * | 6/1998 | Yoshida et al. ...................... 400/708 |

FOREIGN PATENT DOCUMENTS

| | | |
|---|---|---|
| 0 710 569 A1 | 5/1996 | (EP) . |
| 95 323 | 9/1995 | (FI) . |

OTHER PUBLICATIONS

Bradford et al; An on–line sensor for the measurement of paper colour; Appita; Mar., 1991; pp 139–143; vol. 44, No. 2.

* cited by examiner

*Primary Examiner*—Richard A. Rosenberger
(74) *Attorney, Agent, or Firm*—Alston & Bird LLP

(57) ABSTRACT

The invention relates to a method and apparatus for measuring paper color. Paper color is measured from the surface of a paper roll on a winder. As the size of the paper roll grows, a measuring device is moved in such a way that the angle between the measuring device and the surface of the paper roll is kept substantially constant and, at the same time, the distance of the measuring device from the surface of the paper roll remains substantially constant

11 Claims, 2 Drawing Sheets

METHOD AND APPARATUS FOR MEASURING PAPER COLOR

CROSS-REFERENCE TO RELATED APPLICATIONS

This application is a continuation of pending PCT International Application PCT/FI98/00770, filed Sep. 29, 1998, designating inter alia the United States.

FIELD OF THE INVENTION

The invention relates to a method for measuring paper color, whereby paper color is measured from the surface of a paper roll on a winder during the winding of the paper in such a way that the angle between a measuring device and the surface of the paper roll is kept substantially constant.

BACKGROUND OF THE INVENTION

The invention further relates to an apparatus for measuring paper color, the apparatus comprising a measuring device which is arranged to measure paper color from the surface of a paper roll on a winder during, the winding of the paper, and to means for keeping the angle between the measuring device and the paper roll constant.

The article "An on-line sensor for the measurement of paper colour" in the publication "Appita Vol. 44 No. 2" describes a method and apparatus in which paper color is measured on the winder. In this case the caliper of the paper to be measured and its background color cannot affect the measurement result because a thick layer of paper is very quickly formed on the winder, and the paper provides for the color measurement an even backing which also has the same color as the sample to be measured. The measuring device is immovably arranged at a distance from the winder, therefore background light easily interferes too much with the measurement result, and the measuring device is also difficult to calibrate. As the circumference of the paper roll grows, distance to the roll surface must be measured and the measurement angle adjusted on the basis of the measurement, which makes the apparatus complex and cumbersome. Further, the growing circumference of the paper roll changes the distance between the measuring device and the paper surface, which in turn changes the measurement geometry of the apparatus, i.e., the focusing of a light beam directed from the measurement apparatus on the surface of the paper, whereby the measurement provided is inaccurate.

An object of the invention is to provide a method and apparatus allowing the above mentioned drawbacks to be avoided.

SUMMARY OF THE INVENTION

The method of the invention is characterized in that as the size of the paper roll grows, a measuring device is moved in such a way that the distance of the measuring device from the surface of the paper roll remains substantially constant.

The apparatus of the invention is further characterized in that the apparatus comprises means for keeping the distance of the measuring device from the surface of the paper roll constant as the size of the paper roll grows.

An essential idea of the invention is that paper color is measured on a winder, the angle between a measuring device and the paper surface remaining substantially constant and the measuring device being moved, as the roll size grows, in such a way that the distance of the measuring device from the roll surface also remains substantially constant. An idea of a preferred embodiment is that the measuring device is arranged to move in line with the central axis of the roll. An idea of another preferred embodiment is that the measuring device is arranged to move in relation to two joints in such a way that as the roll size grows the measuring device turns, thus keeping the measurement angle substantially constant.

An advantage of the invention is that since paper is very quickly formed on the winder, the paper provides for the color measurement an even surface which also has the same color as the sample to be measured. In this case neither the backing nor the opacity of the paper to be measured affects the result of the color measurement. In addition, because the distance of the measuring device from the paper on the roll surface is small, the disturbing effect of background light can be eliminated and an accurate measurement is obtained. Likewise, the measurement geometry remains unchanged. In addition, since the measuring device moves as the roll size grows, the angle between the measuring device and the paper surface is simple to adjust. The measuring device being arranged to move in line with the central axis of the roll, the measurement angle can be kept constant all the way without turning the measuring device. The invention is particularly well suited for measuring the color of thin paper grades.

BRIEF DESCRIPTION OF THE DRAWINGS

The invention will be described in greater detail in the accompanying drawings in which.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
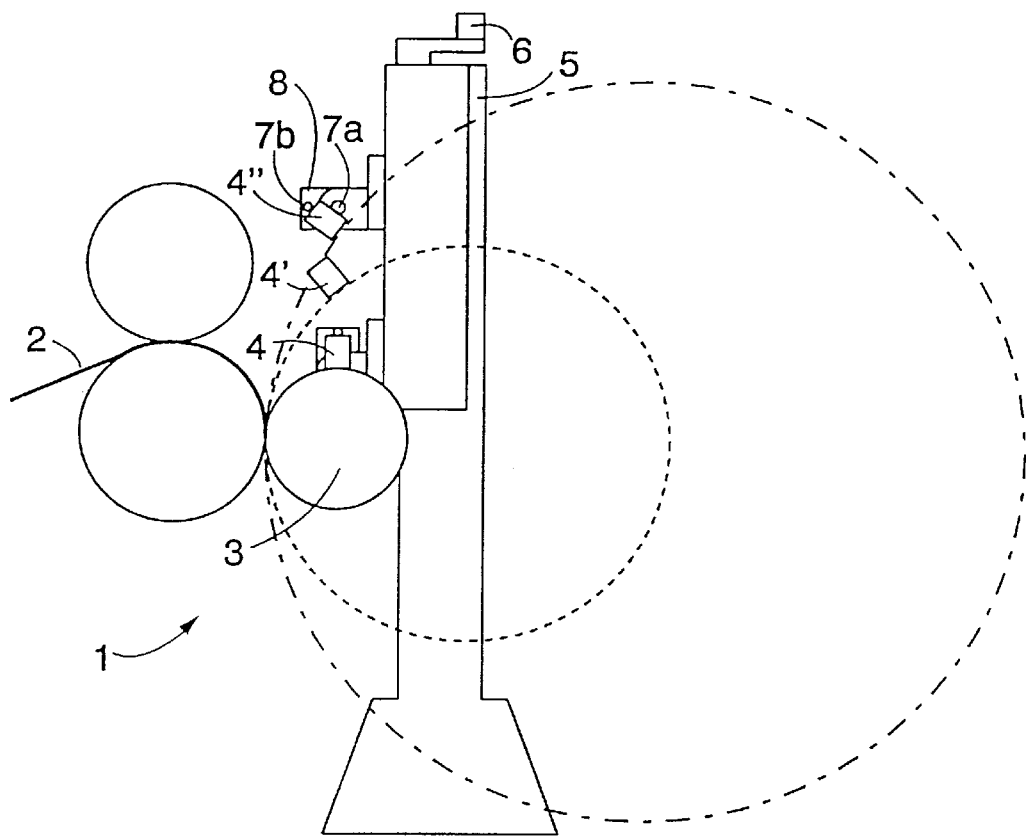
FIG. 1 schematic side view of a measurement arrangement according to the invention.

FIG. 1 illustrates a winder 1 winding paper 2 produced by a paper machine on a roll 3. For the sake of clarity, support structures of the roll 3 are not shown in FIG. 1. A measuring device 4 is arranged to measure the color of the paper 2 from the surface of the roll 3. The measuring device 4 is arranged to move vertically on a beam 5, controlled by a motor 6. As the size of the roll 3 grows the measuring device 4 is lifted upwards.

A continuous line illustrates an empty roll 3. A line of dots and dashes, in turn, illustrates the outlines of the roll 3 when the roll is full. A dashed line illustrates the outlines of the roll 3 with some paper wound on the roll. As the amount of paper on the roll 3 increases, the measuring device 4 is arranged to turn in such a way that the angle of the measuring device in relation to the paper on the surface of the roll 3 remains unchanged. Reference numeral 4' illustrates the position of the measuring device when there is some paper on the roll 3 but it is not yet full. For the sake of clarity, the illustration in FIG. 1 does not show the support structures of the measuring device. Reference numeral 4" illustrates the position of the measuring device when the roll 3 is full.

The apparatus comprises, arranged to the beam 5, a support beam 8 pivotably arranged in relation to a first joint 7a, the support beam being, in turn, provided with the measuring device 4 pivotably arranged in relation to a joint 7b. The joints 7a and 7b allow the angle of the measuring device 4 in relation to the surface of the roll 3 to be kept substantially constant. For the sake of clarity, control devices for controlling the turning of the support beam 8 and the measuring device 4 are not shown in FIG. 1. The measuring device 4 is provided with distance sensors which allow a desired measurement distance to be kept as the paper roll grows. As the roll 3 grows, the measuring device 4 moves according to FIG. 1, maintaining a constant distance from the surface of the roll 3. The turning angles of the support beam 8 and the measuring device 4 each correspond to a particular vertical position of the measuring device 4, the angles in question thereby being easy to determine in the system as functions of the measuring device height, which makes a relatively simple control system possible. Paper color is thus measured when paper 2 is wound with the winder 1. The measurement advantageously takes place during the paper making process, although it can also be carried out in connection with other phases, during the winding of the paper 2 after a separate coating phase, for example.

Figure 2:
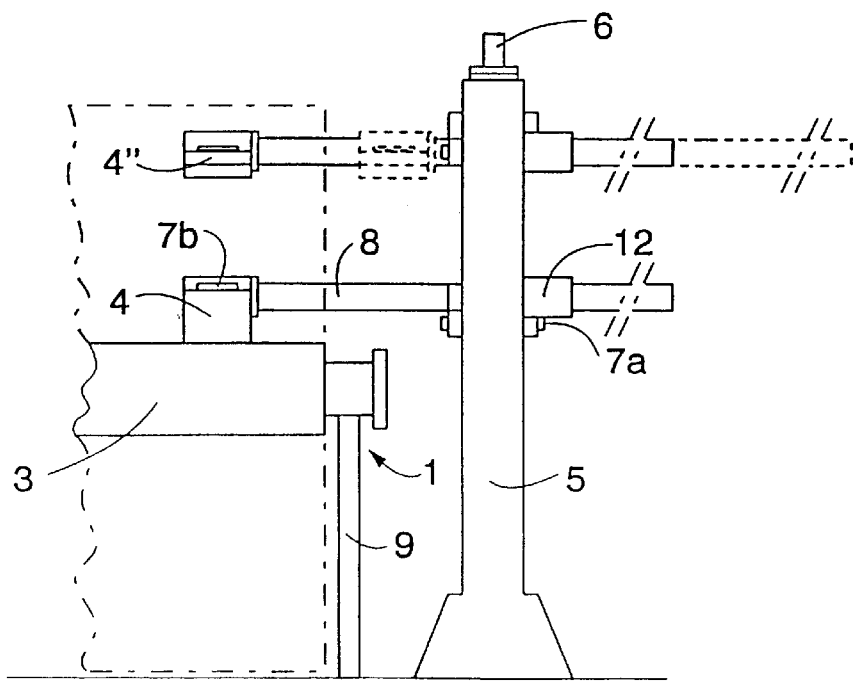
FIG. 2 illustrates the measurement arrangement of FIG. 1 seen from the rear of a paper machine.

FIG. 2 shows the arrangement of FIG. 1 seen from the rear of the paper machine. FIG. 2 shows an empty roll 3 and the outlines of the roll 3 when it is full, illustrated with a line of dots and dashes. FIG. 2 further shows support structures 9 of the winder 1. The apparatus shown in FIGS. 1 and 2 requires fairly little space, so it is easy to arrange in connection with a paper machine winder.

For instance, in web break situations and when paper is packed on the surface of the paper roll 3, the distance sensors issue a command to move the measuring device 4 away from the roll 3 by impact of a motor 12 to a position shown with a dashed line in FIG. 2. Information about a web break can also be brought to the apparatus from the outside. The measuring device 4 can also be guided to the position shown with the dashed line for the duration of roll change and/or standardization and/or calibration. For standardization and calibration a fixed head of the color meter can be arranged at a point shown with a dashed line in FIG. 2. Standardization, for example, can therefore be carried out at the point in question about once an hour when the roll becomes full and the measuring device 4 must therefore be moved to the point in question anyway. By means of the motor 12 the measuring device 4 can also be made to move back and forth along the surface of the roll 3, transversely to the moving direction of the paper 2, i.e., parallel to the axis of the roll 3. The measurement can thus be taken, when desired, at any point of the roll 3 and, in addition, the measurement can be carried out in such a way that as the measuring device 4 moves back and forth, it continuously measures substantially the entire area of the roll 3. The support beam 8 can also extend over the entire width of the paper to be wound. The measuring device 4 then moves back and forth along the support beam 8 and the measurement is performed as a continuous measurement, as described above.

Figure 3:
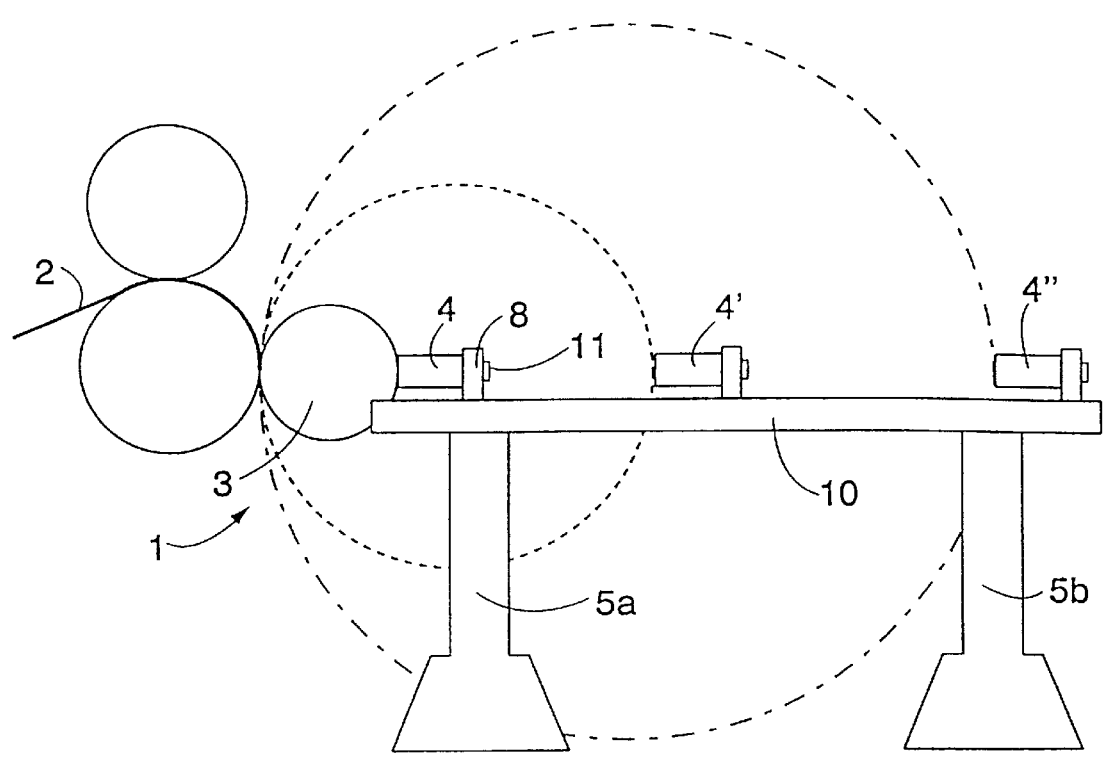
FIG. 3 is schematic side view of another measurement arrangement of the invention.

FIG. 3 illustrates another measurement arrangement according to the invention. The measuring device 4 and the support beam 8 are in this application arranged to move along a slide beam 10 arranged on beams 5a and 5b. The measuring device 4 is arranged to measure perpendicularly to the surface of the roll 3 and to move in line with the movement of the central axis of the roll when the roll 3 is filled. In this case, as the roll 3 grows bigger, the angle of the measuring device 4 need not be changed, instead it is sufficient that the measuring device 4 is only moved along the slide beam 10.

Figure 4:
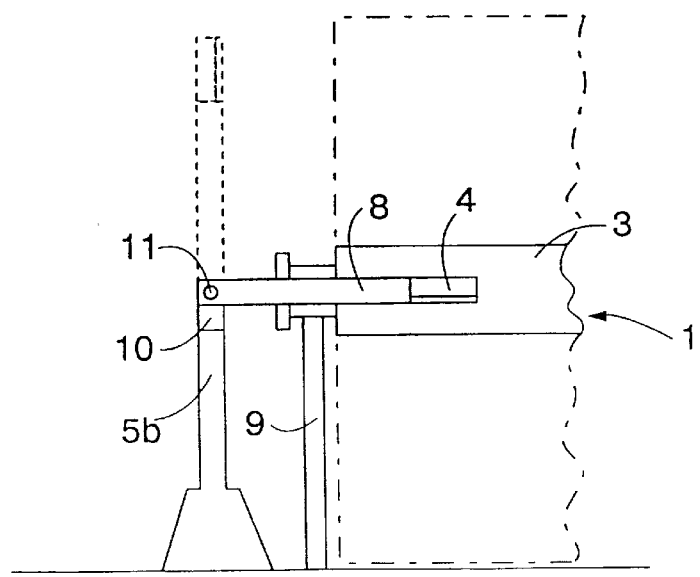
FIG. 4 illustrates the measurement arrangement of FIG. 3 seen from the rear of the paper machine.

FIG. 4 shows a solution according to FIG. 3, seen from the rear of the paper machine. The support beam 8 is arranged to turn in relation to a joint 11. The support beam 8 and the measuring device 4 can then be turned to a position shown with a dashed line in FIG. 4, e.g., in web break situations, for the duration of roll change or for standardization or calibration.

The measuring device 4 can be placed above the roll 3 at a distance of for instance about 0.5 meters from the edge, thereby avoiding measurement of the edge zone, which does not represent full paper quality. The measurement geometry of the measuring device 4 can be for instance 45°/0°, as is known per se, which means that the angle of incidence of light is 45° and paper color is measured perpendicularly to the paper surface. The distance of the measuring device from the paper surface can then be less than 10 mm, most preferably less than 5 mm. A typical distance in this case is 3 mm±0.1 mm. Other type of geometry is also possible in the measuring device 4, the distance of the measuring device 4 from the paper surface then being possibly even longer. An essential feature is that by means of the measuring device structure and distance the preventing of diffused light has been taken into consideration in the apparatus, diffused light thus having no essential influence on the measurement result.

The drawings and the related description are only meant to illustrate the inventive idea. The details of the invention may vary within the scope of the claims.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for measuring the color of paper during a winding operation of a paper roll in a winder, the method comprising:

positioning a measuring device at a predetermined distance from an outer surface of a paper roll;

positioning the measuring device to define a predetermined angular relationship with the outer surface of the paper roll;

moving the measuring device so as to maintain the distance and the angular relationship between the measuring device and the paper roll constant as the paper roll changes diameter during the winding operation.

2. A method according to claim 1 wherein the measuring device moving step further comprises turning the measuring device around at least two joints to maintain the angle of the measuring device constant in relation to the surface of the paper roll.

3. A method according to claim 1 wherein the measuring device moving step further comprises moving the measuring device in line with the movement of the central axis of the paper roll.

4. A method according to claim 1 wherein the measuring device moving step comprises maintaining the distance of the measuring device from the surface of the paper roll at less than 10 mm.

5. A method according to claim 1 further comprising the step of moving the measuring device back and forth transversely in relation to the moving direction of the paper during the measuring operation.

6. An apparatus for measuring the color of paper during a winding operation of a paper roll in a winder, the apparatus comprising:

a measuring device which is positioned at a predetermined distance from an outer surface of a paper roll, said measuring device defining a predetermined angular relationship with the outer surface of the paper roll;

means for maintaining the angular relationship between the measuring device and the surface of the paper roll constant as the paper roll changes diameter during the winding operation; and means for maintaining the distance between the measuring device and the paper roll constant as the paper roll changes diameter during the winding operation.

7. An apparatus according to claim 6 wherein the means for maintaining the angular relationship constant further comprises;

a beam;

a support beam pivotably supported on the beam by way of a first joint; and a second joint for pivotably supporting the measuring device on the support beam.

8. An apparatus according to claim 6 wherein the means for maintaining the distance constant further comprises a slide beam on which the measuring device is slidably supported such that the measuring device can be moved in line with the movement of the central axis of the paper roll.

9. An apparatus according to claim 6 wherein the predetermined distance between the measuring device and the surface of the paper roll is less than 10 mm.

10. An apparatus according to claim 6 further comprising means for moving the measuring device away from the paper roll.

11. An apparatus according to claim 6 further comprising means for moving the measuring device back and forth transversely in relation to the moving direction of the paper.

* * * * *

UNITED STATES PATENT AND TRADEMARK OFFICE
CERTIFICATE OF CORRECTION

PATENT NO.   : 6,297,882 B1
DATED        : October 2, 2001
INVENTOR(S)  : Moisio It is certified that error appears in the above-identified patent and that said Letters Patent is hereby corrected as shown below:

<u>Title page,</u>
Item [30], Foreign Application Priority Data, "Jan. 10, 1997" should read
-- Oct. 1, 1997 --.

Signed and Sealed this

Second Day of July, 2002

Attest:

Attesting Officer

JAMES E. ROGAN
*Director of the United States Patent and Trademark Office*